United States Patent
Anjum

(10) Patent No.: US 10,182,533 B2
(45) Date of Patent: Jan. 22, 2019

(54) SYSTEMS AND METHODS FOR RECOMMENDING A PLANT SELECTION

(71) Applicant: GroGuru, Inc., San Diego, CA (US)

(72) Inventor: Farooq A. Anjum, San Diego, CA (US)

(73) Assignee: GroGuru, Inc., San Diego, CA (US)

( * ) Notice: Subject to any disclaimer, the term of this patent is extended or adjusted under 35 U.S.C. 154(b) by 165 days.

(21) Appl. No.: 14/813,087

(22) Filed: Jul. 29, 2015

(65) Prior Publication Data

US 2016/0029568 A1 Feb. 4, 2016

Related U.S. Application Data

(60) Provisional application No. 62/030,559, filed on Jul. 29, 2014, provisional application No. 62/030,566, filed on Jul. 29, 2014, provisional application No. 62/030,568, filed on Jul. 29, 2014, provisional application No. 62/030,573, filed on Jul. 29, 2014.

(51) Int. Cl.

| | | |
|---|---|---|
| *G01V 3/00* | (2006.01) |
| *A01G 22/00* | (2018.01) |
| *A01G 25/16* | (2006.01) |
| *G05B 15/02* | (2006.01) |
| *G01N 27/04* | (2006.01) |
| *G01N 27/22* | (2006.01) |

(52) U.S. Cl.
CPC ............. *A01G 22/00* (2018.02); *A01G 25/16* (2013.01); *A01G 25/167* (2013.01); *G01N 27/048* (2013.01); *G01N 27/221* (2013.01); *G01N 27/223* (2013.01); *G05B 15/02* (2013.01)

(58) Field of Classification Search
CPC ...... A01G 1/001; A01G 25/16; A01G 25/167; G01N 27/048; G01N 27/221; G01N 27/223
USPC .......................................................... 702/2
See application file for complete search history.

(56) References Cited

U.S. PATENT DOCUMENTS

| | | | |
|---|---|---|---|
| 7,162,438 B1 * | 1/2007 | Kelly | ............... G06Q 10/06315 705/7.25 |
| 2007/0284552 A1 | 12/2007 | Khorshid | |
| 2013/0174040 A1 * | 7/2013 | Johnson | ................. G06Q 10/06 715/733 |

* cited by examiner

*Primary Examiner* — Caleb Henry
(74) *Attorney, Agent, or Firm* — Hojka Qadeer, LLC; Cory L. Hojka

(57) ABSTRACT

A remote platform receives plant selection criteria and determines a plant selection based on the plant selection criteria. The plant selection criteria may include a plant preference, a budget preference, and garden parameters measured by sensors in a garden.

14 Claims, 7 Drawing Sheets

SYSTEMS AND METHODS FOR RECOMMENDING A PLANT SELECTION

CROSS-REFERENCE TO RELATED APPLICATIONS

This application claims the benefit of, and priority to, U.S. Provisional Patent Application Ser. Nos. 62/030,559, filed Jul. 29, 2014; 62/030,566, filed Jul. 29, 2014; 62/030,568, filed Jul. 29, 2014; and 62/030,573, filed Jul. 29, 2014; the entire disclosures of which are incorporated herein by reference.

BACKGROUND

Field of the Invention

The embodiments described herein generally relate to the field of electronic information management, and more particularly to the dynamic collection, analysis, and regulation of various garden parameters.

Description of the Related Art

As of 2011, the global gardening and outdoor living industry was already worth a staggering $187 billion. In North American alone, sales of plants, seeds, and other garden paraphernalia reached nearly $58 billion. These statistics are compelling evidence of mankind's affinity toward verdant foliage and vibrant blossoms. Indeed, many millions of Americans, whether or not they consider themselves gardening enthusiasts, are engaged in some form of lawn care and gardening activities. There are tens of millions of acres of residential lawns in the United States. Even households that do not have access to residential lawns are keen to install planters, and to find alternative, smaller scale ways to cultivate plants both indoors and outdoors.

But maintaining a garden has also become an increasingly difficult and unattainable endeavor in recent years. For one, global climate changes have made it harder to create and sustain the various conditions required for different plants to survive. While weather conditions (e.g., temperature, sunlight, and rainfall) often fluctuate outside of historical norms and sometimes to extremes, plants typically need very steady and specific levels of moisture, heat, and light exposure. Consequently, even seasoned horticulturists are struggling to create and maintain ideal plant habitats. Furthermore, gardening is also now a much more costly pursuit. Many regions around the world experience severe and chronic drought conditions, and water has become a more precious commodity than ever before. The rates for water in the United States, for instance, have increased drastically in recent years (e.g., 75% between 2000 and 2012) as have the fines and penalties for over- and misusage of water. Meanwhile, the water shortages that plague many parts of the country, such as California, are not expected to abate any time soon.

Temperamental weather and soaring water costs are just a few of the challenges that overwhelm conventional gardening methods. Under- and overwatering, for example, are a persistent and pricey problem because most households program their sprinkler systems according to a static schedule or frequency, causing plants to be watered regardless of current moisture levels in the soil or imminent rainfall. In addition, gardens tend to be individually unique ecosystems, although the differences are often incredibly nuanced and hardly perceptible to the average person. Very often, a plant that flourishes in one location will mysteriously flounder in another. Alice, for example, can fail to grow peonies in her garden even though the same type of plant thrives in her neighbor Bob's yard. This is because conventional approaches to gardening disregard particularized and real-time data with respect to each individual garden ecosystem. Plant care guidelines, which are typically found on placards that accompany commercially available plants, provide only very general recommendations (e.g., light exposure, type of fertilizer, and watering and feeding frequency). But based on these types of instructions alone, it is still virtually impossible to systematically recreate an ideal growing environment. So more often than not, for the average person, successfully growing a plant often entails an interminable and frustrating succession of trial and error.

SUMMARY

Systems and methods for dynamically collecting, analyzing, and regulating garden parameters are described herein. These and other features, aspects, and embodiments are described below.

BRIEF DESCRIPTION OF THE DRAWINGS

Features, aspects, and embodiments are described in conjunction with the attached drawings.

DETAILED DESCRIPTION

The invention may be implemented in numerous ways, including but not limited to implementation as a process; an apparatus; a system; a composition of matter; a computer program product embodied on a computer readable storage medium; and a processor, such as a processor configured to execute instructions stored on or provided by a memory coupled to the processor. These implementations, or any other embodiments, may be referred to as techniques. In general, the order of the steps of disclosed processes may be altered unless specified otherwise or otherwise clear from context. Unless stated otherwise, a component such as a processor or a memory described as being configured to perform a task may be implemented as a general component that is temporarily configured to perform the task at a given time or a specific component that is manufactured to perform the task. As used herein, the term "processor" refers to one or more devices, circuits, or processing cores configured to process data, such as computer program instructions.

A detailed description of one or more embodiments is provided below along with accompanying figures. The invention is described in connection with such embodiments, but the invention is not limited to any specific embodiment. The scope of the invention is limited only by the claims and the invention encompasses numerous alternatives, modifications, and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Setup and Configuration

Figure 1:
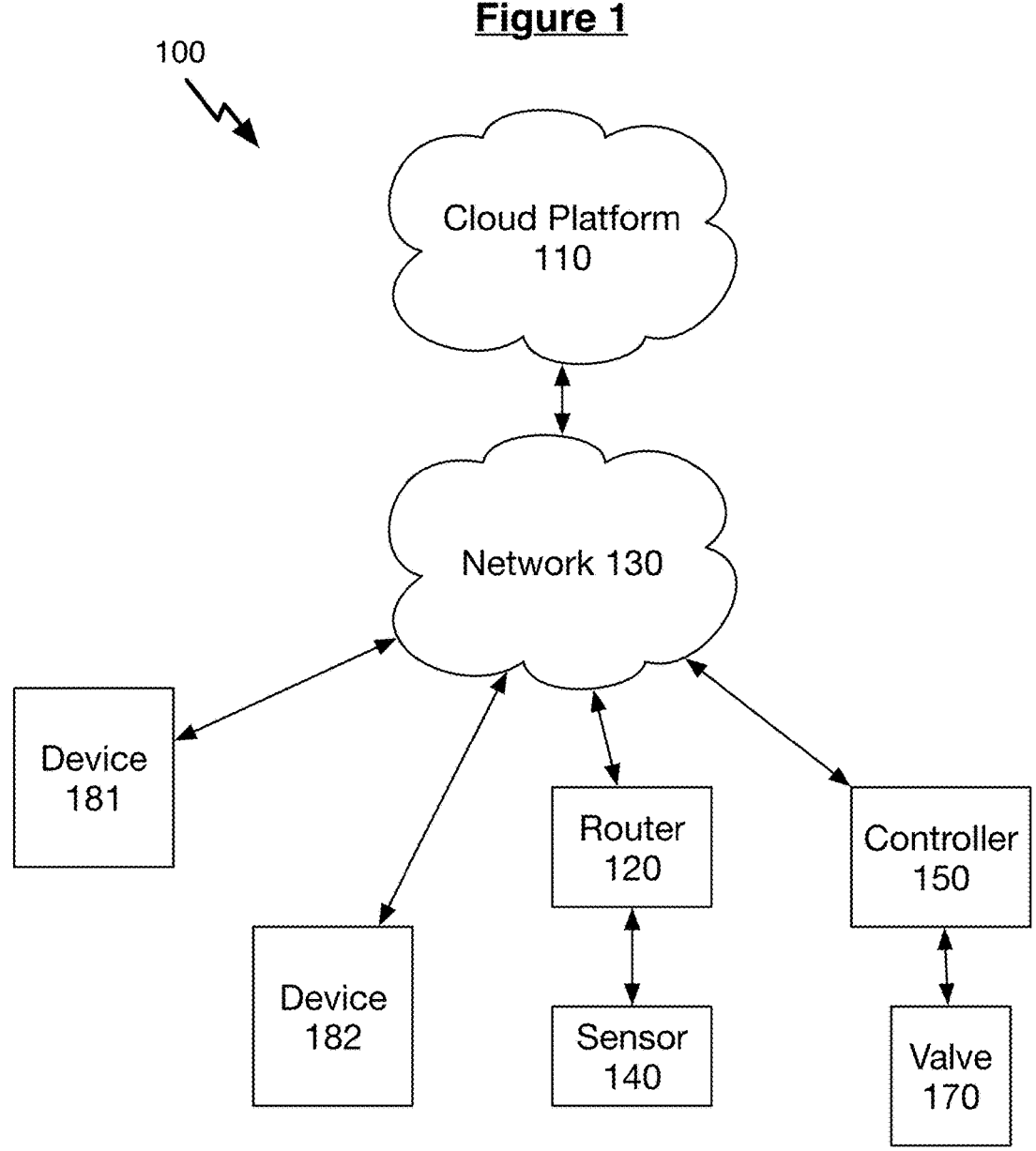
FIG. 1 is a diagram illustrating an embodiment of a system for dynamically collecting, analyzing, and regulating garden parameters.

FIG. 1 is a diagram illustrating an embodiment of a System 100 for dynamically collecting, analyzing, and regulating garden parameters. Although the term "garden" is used throughout, it is to be understood that the systems and methods described herein are applicable to and can be used in any area or location where plants are grown or to be grown, including but not limited to orchards, lawns, nurseries, planters, fields, parks, etc. As shown in FIG. 1, in some of the embodiments described herein, System 100 may comprise a Cloud Platform 110, which may communicate with a Router 120 via Network 130. In various embodiments, Network 130 may be the Internet, and can include wireless and wired WANs, LANs, or PANs. In some of the embodiments described herein, Router 120 may also communicate with Sensor 140 or Controller 150. In various embodiments, Router 120 may communicate with Sensor 140 or Controller 150 via a wireless connection. In various embodiments, Router 120 may communicate with Sensor 140 or Controller 150 using a WiFi connection. It is to be understood that in various other embodiments of System 100 not shown in FIG. 1, Router 120 may communicate with any appropriate, required, or desired number (e.g., two or more) of sensors (e.g., Sensor 140) or controllers (e.g., Controller 150). It is also to be understood that Controller 150 is optional and in some embodiments of System 100 not shown in FIG. 1, System 100 may operate without Controller 150. Finally, it is to be understood that, in various embodiments, the functionalities of Sensor 140 and Controller 150 may be integrated into a single hybrid device or apparatus.

In various embodiments, Sensor 140 may be configured to take one or more measurements in order to generate Data 160. For example, in various embodiments, Sensor 140 may be capable of measuring temperature, light, and moisture. Meanwhile, in various embodiments, Data 160 may include at least one real time garden parameter, including but not limited to soil moisture, soil salinity, soil temperature, soil pH, external temperature, external humidity, and light exposure. In various embodiments, Sensor 140 may be configured to take measurements according to a predetermined or to a dynamic schedule or frequency. Furthermore, in various embodiments, Sensor 140 may also be configured to transmit Data 160 to Router 120. In some embodiments, Data 160 may be transmitted to Router 120 in real time. In other embodiments, Data 160 may be transmitted to Router 120 at preset intervals (e.g., hourly, daily, weekly) or at variable intervals, which can change dynamically based on one or more factors such as user input or the frequency of measurements taken by Sensor 140.

In some embodiments, Controller 150 may be configured to control sprinkler Valve 170. In various embodiments, Controller 150 may receive signals from Router 120 that includes commands or instructions to open and to close Valve 170. In various embodiments, based on the instructions from Router 120, Controller 150 may then instruct Valve 170 to open or to close. In some embodiments, Valve 170 may be a solenoid valve, a type of valve that is commonly found in various residential and commercial sprinkler systems. In some embodiments, Controller 150 may be particularly well suited to controlling solenoid valves. In some embodiments, Controller 150 may directly cause Valve 170, a solenoid valve, to open and to close by modulating the electric current that controls the valve. Thus, in some embodiments, Controller 150 does not operate by regulating the water supply to Valve 170, but rather by modulating an electric current. Advantageously, in some embodiments, since Controller 150 may modulate the electric signals instead of the water flow to Valve 170, Controller 150 may be installed quickly and effortlessly without disrupting any of the existing pipelines connected to Valve 170. In some embodiments, Controller 150 may be installed as an addition to an existing, conventional sprinkler controller system. In various embodiments, Controller 150 and Valve 170 may be integrated into a single hybrid device or apparatus.

In various embodiments, Router 120 may be configured to communicate with Cloud Platform 110 through Network 130. In various embodiments, Router 120 may be configured to transmit data to Cloud Platform 110. As discussed earlier, in various embodiments, Router 120 may receive Data 160 (e.g., garden parameters) from Sensor 140. In various embodiments, Router 120 may then transmit Data 160 to Cloud Platform 110. In various embodiments, Router 120 may also be configured to receive Data 161 from Cloud Platform 110. As discussed earlier, Router 120 may transmit signals to Controller 150. In particular, Router 120 may transmit signals directing Controller 150 to cause Valve 170 to open and to close. In various embodiments, Router 120 may transmit to Controller 150 signals which it receives from Cloud Platform 110. In various embodiments, Cloud Platform 110 may analyze data, such as Data 160, in order to determine or to generate Data 161. For example, in some embodiments, Cloud Platform 110 may analyze various garden parameters (e.g., soil moisture, soil salinity, soil temperature, soil pH, external temperature, external humidity, light exposure) to determine whether or when to turn on (or off) Valve 170. In various embodiments, Data 161 may include data that is generated by applying one or more statistical analysis techniques to Data 160, including but not limited to extrapolating, interpolating, averaging, or segmenting Data 160. In some embodiments, Cloud Platform 110 may further receive Data 162. In various embodiments, Data 162 may come from any appropriate source or sources, and may include additionally relevant data such as the weather forecast. In some embodiments, Data 162 may include historical data and collective data (e.g., past or present garden parameters from multiple users). In some embodiments, Data 161 may include possible future garden parameters forecasted based at least in part on Data 160 and Data 162. In various embodiments, Data 162 may also include user inputs, such as instructions, commands, and any other appropriate types of user feedback. For example, in various embodiments, users may be able to input and transmit to Cloud Platform 110 real life observations (e.g., moistness of the soil, health of plants) and, as will be discussed in more detail below, preferences (e.g., preferred plants, budgets). In various embodiments, Cloud Platform 110 may generate or determine Data 161 based on an analysis of one or both of Data 160 and Data 162.

In addition to Router 120, FIG. 1 further shows that in various embodiments, Cloud Platform 110 may also communicate with Device 181 and Device 182 via Network 130.

In various embodiments, Devices 181 and 182 may be any appropriate type of computing and communication device, including but not limited to a smartphone, tablet PC, or personal computer. In various embodiments, Device 181 and Device 182 may each be capable of hosting Application 190. For example, in some embodiments, users may download and install Application 190 onto their respective devices of choice (e.g., Device 181, Device 182). In various embodiments, Application 190 may allow various users to communicate with Cloud Platform 110, including by sending, receiving, and otherwise interacting with various types of data. In particular, in some embodiments, Cloud Platform 110 may be capable of collecting and analyzing data, such as Data 160, from different gardens and over extended periods of time. In addition, in some embodiments, Cloud Platform 110 may keep track of the current status of one or both of Controller 150 and Valve 170. Thus, in various embodiments, users may use Application 190 to interact with (e.g., view) current, historical, and collective sets of data.

In various embodiments, users may also use Application 190 to see the current status of their respective sprinkler systems (e.g., is Valve 170 open or closed). In various embodiments, Cloud Platform 110 may transmit one or more alerts, notifications, or recommendations to the user via Application 190. For example, based on Data 160 (e.g., garden parameters measured by Sensor 140) and Data 162 (e.g., historical data and collective data from different users, weather, forecasted garden parameters, user inputs, etc.), Cloud Platform 110 may generate and transmit to the user an alert, notification, or recommendation that instructs the user to perform one or more actions in order to achieve certain garden parameters. In various embodiments, Cloud Platform 110 may recommend actions such as adding additives (e.g., fertilizers to change the pH or salinity in the soil), applying mulch (e.g., to control moisture level and soil temperature), and covering the plants (e.g., to encourage a more humid environment).

In some embodiments, Application 190 may provide one or more options for users to change or to override the current status of their respective sprinkler systems. That is, in some embodiments, a user may request, through Application 190, that Controller 150 force shuts Valve 170. However, as described earlier, it is to be understood that System 100 may, in various embodiments, also operate without Controller 150. In some embodiments, Controller 150 is optional equipment. In those embodiments where Controller 150 is not installed or is not in use, instead of sending commands or instructions to Controller 150 to turn on (and off) Valve 170, Cloud Platform 110 may transmit alerts, notifications, or recommendations to Device 181 or Device 182 instructing the user to manually turn on (and off) Valve 170.

Sprinkler systems are typically installed based on a multizone paradigm. That is, a planted area (e.g., garden, lawn, field, golf course) is divided into different zones and each sprinkler valve (or group of sprinkler valves) in the sprinkler system is designated to service a separate zone. Since each sprinkler valve (e.g., Valve 170) may require a separate controller (e.g., Controller 150) in the various embodiments of System 100 described with respect to FIG. 1, System 100 is ideally suited for a planted area with a relatively small number (e.g., two or fewer) zones. However, System 100 may nonetheless be used for a planted area with any number of zones.

Figure 2:
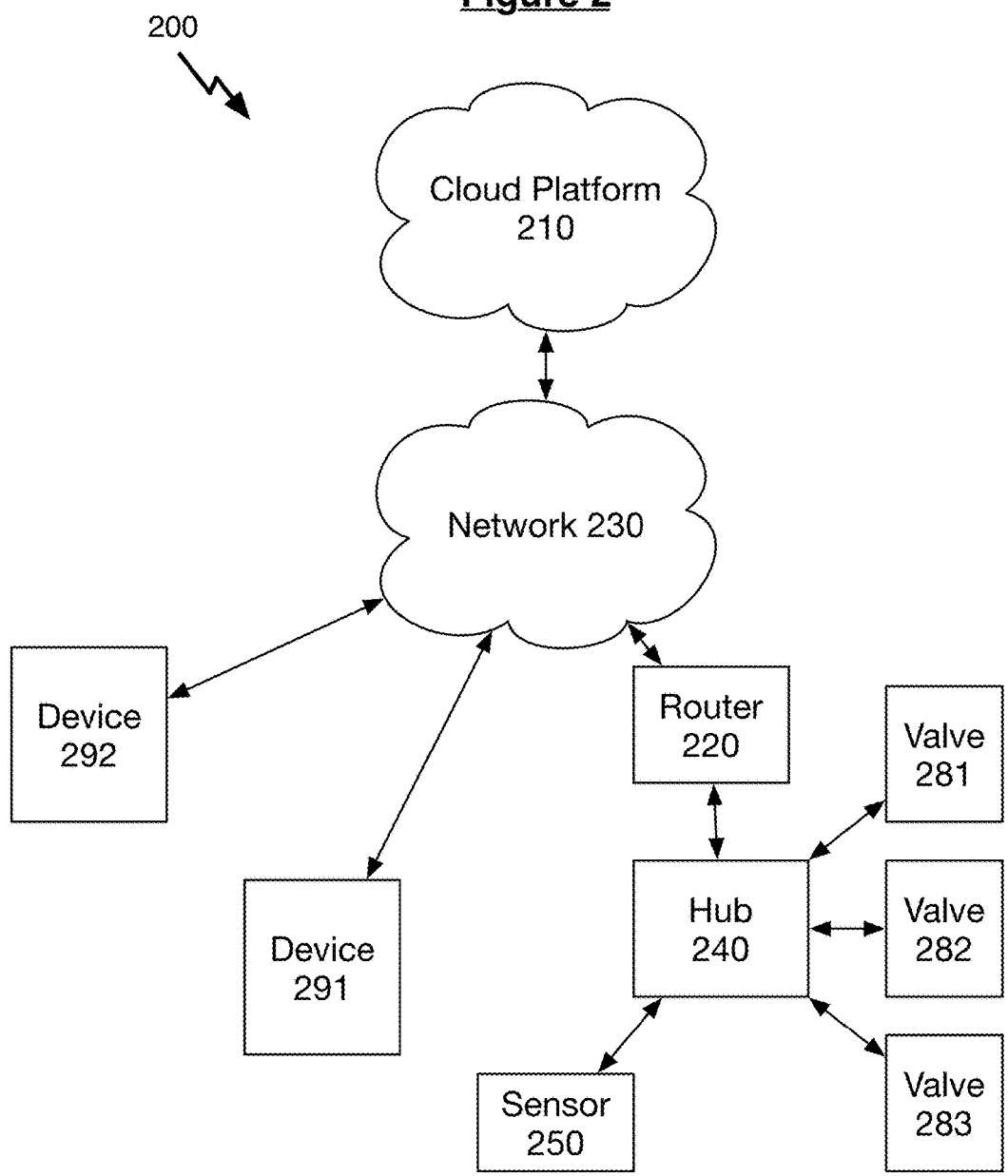
FIG. 2 is a diagram illustrating an embodiment of a system for dynamically collecting, analyzing, and regulating garden parameters.

FIG. 2 is a diagram illustrating an embodiment of a System 200 for dynamically collecting, analyzing, and regulating garden parameters. In various embodiments, System 200 is ideally suited for a planted area with a larger number of zones (e.g., more than two), though it may also be used for a planted area with fewer zones. As shown in FIG. 2, in some of the embodiments described herein, System 200 may comprise a Cloud Platform 210, which may communicate with a wireless Router 220 via Network 230. Meanwhile, according to FIG. 2, in some of the embodiments described herein, Router 220 may further communicate with a Hub 240. In various embodiments, Hub 240 may be WiFi-enabled and may communicate with Router 220 via a WiFi link. In various embodiments, Hub 240 may also communicate with Sensor 250. In various embodiments, Hub 240 and Sensor 250 may be capable of communicating over a low-power, sub-GHz link. In some embodiments, Hub 240 may communicate with Sensor 250 via a 900 MHz long distance radio link. In contrast to System 110, which was described with respect to FIG. 1, in various embodiments of System 200, Sensor 250 may not be required to communicate directly with Router 220 over a WiFi link. Instead, in various embodiments of System 220, Hub 240 may act as a broker or intermediary that centralizes the communication of various types of data between Router 220 and Sensor 250. In the various embodiments of System 200, Sensor 250 may only be required to communicate data over a low-power sub-GHz link. Advantageously, in the various embodiments of System 200, Sensor 250 may be more power efficient than a WiFi enabled counterpart, such as Sensor 140 described with respect to FIG. 1. It is to be understood that, although not shown in FIG. 2, in various other embodiments of System 200, Hub 240 may communicate with any appropriate, necessary, or desired number (e.g., two or more) of sensors (e.g., Sensor 250). It is also to be understood that Hub 240 is optional and in some embodiments of System 200 not shown in FIG. 2, System 200 operates without Controller 150.

In various embodiments, Sensor 250 may communicate with Hub 240 including by transmitting Data 260 to Hub 240. In various embodiments, Data 260 may be generated by Sensor 250 based on or using one or more measurements taken by Sensor 250 (e.g., temperature, humidity, light). In various embodiments, Data 260 may include at least one real time garden parameter, including but not limited to soil moisture, soil salinity, soil temperature, soil pH, external temperature, external humidity, and light exposure. In various embodiments, Sensor 250 may be configured to take measurements according to a predetermined or to a dynamic schedule or frequency, and to transmit Data 260 to Hub 240 in real time or at preset intervals (e.g., hourly, daily, weekly) or at variable intervals, which can change dynamically based on one or more factors such as user input or the frequency of measurements taken by Sensor 140.

In various embodiments, Hub 240 may be used instead of or in place of a conventional sprinkler control system because Hub 240 may be capable of controlling multiple sprinkler valves in a sprinkler system. This is in contrast to the various embodiments of System 100 wherein each valve (e.g., Valve 170) may require a separate controller (e.g., Controller 150). As FIG. 2 illustrates, Hub 240 may control the operations (e.g., opening and closing) of Valves 281, 282, and 283. However, it is to be understood that in various embodiments, Hub 240 may control any appropriate, required, or desired number of valves. In various embodiments, Hub 240 may be capable of opening (or closing) some or all of Valves 281, 282, and 283 including by determining and transmitting one or more control signals to the appropriate valve(s). In various embodiments, Hub 240 may determine which of Valves 281, 282, and 283 to open (or close) and when based at least in part on Data 261 from Router 220. As will be discussed in more detail below, in various embodiments, Data 261 may originate from Cloud Platform 210. In some embodiments, Data 261 may include explicit commands or instructions for Hub 240 to open (or close) some or all of Valves 281, 282, and 283. In some embodiments, Data 261 may include a fully or partially processed data set. Thus, in various embodiments, it is understood that Hub 240 may be capable of executing instructions (or commands) from Cloud Platform 210 to open (or close) some or all of Valves 281, 282, and 283. Instead or in addition, in some embodiments, Hub 240 may be capable of analyzing a fully or partially processed data set from Cloud Platform 210 in order to generate one or more instructions (or commands) to open (or close) some or all of Valves 281, 282, and 283.

Meanwhile, as discussed earlier, in various embodiments, Hub 240 may be capable of communicating with Cloud Platform 210 through wireless Router 220. In various embodiments, Hub 240 may be a WiFi transceiver that transmits to Router 220 various types of data destined for Cloud Platform 210. For example, as discussed earlier, in some embodiments, Hub 240 may receive Data 260 from Sensor 250 over a sub-GHz (e.g., 900 MHz) link. Thus, in some embodiments, Hub 240 may transmit Data 260, whether immediately or according to a preset schedule or frequency, to Cloud Platform 210 through Router 220. In addition, in some embodiments, Hub 240 may be a WiFi transceiver that receives from Router 220 various types of data, including Data 261, from Cloud Platform 210. In various embodiments, Cloud Platform 210, like Cloud Platform 110 discussed with respect to FIG. 1, may analyze data, such as Data 260, in order to determine or to generate Data 261. In various embodiments, Cloud Platform 210 may analyze various garden parameters (e.g., soil moisture, soil salinity, soil temperature, soil pH, external temperature, external humidity, and light exposure) to determine or to generate Data 261. In various embodiments, Data 261 may include data that generated by applying one or more statistical analysis techniques to Data 260, including but not limited to extrapolating, interpolating, averaging, and segmenting Data 260. In some embodiments, Cloud Platform 210 may further receive Data 262. In various embodiments, Data 262 may come from any appropriate source or sources, and can include additionally relevant data such as the weather forecast. In some embodiments, Data 262 may include historical data and collective data (e.g., past or present garden parameters from multiple users or gardens). As will be discussed in more detail below, Data 262 may also include user inputs, such as instructions, commands, and any type of appropriate user feedback. For example, in various embodiments, users may be able to input and transmit to Cloud Platform 210 real life observations (e.g., moistness of the soil, health of plants) and, as will be discussed in more detail below, preferences (e.g., preferred plants, budgets). In various embodiments, Cloud Platform 210 may generate or determine Data 261 based on an analysis of one or both of Data 260 and Data 262. In some embodiments, Data 261 may include possible future garden parameters forecasted based at least in part on Data 260 and Data 262. In some embodiments, Cloud Platform 210 may analyze one or both of Data 260 and Data 262 to determine whether and when to turn on (or off) some or all of Valves 281, 282, and 283. Thus, in some embodiments, Data 261 may include commands or instructions for Hub 240 to turn on (or off) some or all of Valves 281, 282, and 283. Alternately or in addition, in some embodiments, Cloud Platform 210 may fully or partially analyze one or both of Data 260 and Data 262 and then generate a refined, condensed, edited, or otherwise processed data set based on one or both of Data 260 and Data 261. As such, in some embodiments, Data 261 may include a fully or partially processed data set in addition to or in lieu of instructions (or commands) directed toward some or all of Valves 281, 282, and 283.

In addition to Router 220, FIG. 2 further shows that in various embodiments, Cloud Platform 210 may also communicate with Device 291 and Device 292 via Network 230. In various embodiments, Devices 291 and 292 may be any appropriate type of computing and communication device, including but not limited to a smartphone, tablet PC, or personal computer. In various embodiments, Device 291 and Device 292 may each be capable of hosting Application 293. For example, in some embodiments, users may download and install Application 293 onto their respective devices of choice (e.g., Device 291, Device 292). In various embodiments, Application 293 may allow various users to communicate with Cloud Platform 210, including by sending, receiving, and otherwise interacting with various types of data. In particular, in some embodiments, Cloud Platform 210 may be capable of collecting and analyzing data, such as Data 260, from different gardens and over extended periods of time. In addition, in some embodiments, Cloud Platform 210 may keep track, either directly or via Hub 240, of the current status of Valves 281, 282, and 283. Thus, in various embodiments, users may use Application 293 to interact with (e.g., view) current, historical, and collective sets of data.

In various embodiments, users may also use Application 293 to receive updates on the current status of their respective sprinkler systems (e.g., are some or all of Valves 281, 282, and 283 open or closed). In various embodiments, Cloud Platform 210 may also transmit one or more alerts, notifications, or recommendations to the user via Application 293. For example, based on Data 260 (e.g., garden parameters measured by Sensor 140) and Data 262 (e.g., historical data and collective data from different users, forecasted garden parameters, and user inputs), Cloud Platform 210 may generate and transmit to the user an alert, notification, or recommendation that instructs the user to perform one or more actions in order to achieve certain garden parameters. In various embodiments, Cloud Platform 210 may recommend actions such as adding additives (e.g., fertilizers to change the pH or salinity in the soil), applying mulch (e.g., to control moisture level and soil temperature), and covering the plants (e.g., to encourage a more humid environment).

In some embodiments, Application 293 may provide one or more options for users to change or to override the current status of their respective sprinkler systems. That is, in some embodiments, a user may request, through Application 190, that Hub 240 force shuts some or all of Valves 281, 282, and 283. However, as discussed earlier, it is to be understood that System 240 may, in various embodiments, also operate without Hub 240. In some embodiments, Hub 240 is optional equipment. In those embodiments where Hub 240 is not installed or is not in use, instead of sending commands or instructions to Hub 240 to turn on (and off) some or all of Valves 281, 282, and 283, Cloud Platform 210 may transmit alerts, notifications, or recommendations to Device 281 instructing the user to manually turn on (and off) some or all of Valves 281, 282, and 283.

As discussed earlier, in some embodiments of System 100 described with respect to FIG. 1, at least one sensor (e.g., Sensor 140) and one controller (e.g., Controller 150) may communicate directly with Router 120 via a wireless link (e.g., WiFi). In some embodiments, it is to be understood that System 100 may include any appropriate, required, or desired number of sensors, controllers, and sensor-controller hybrids. As discussed earlier with respect to FIG. 2, in some embodiments of System 200, at least one sensor (e.g., Sensor 250), may communicate directly with a hub (e.g., Hub 240) over a wireless link (e.g., low power, sub-GHz link). As with System 100, in various embodiments of System 200, any appropriate, required, or desired number of sensors may be used. However, particularly in larger gardens, one or more devices may be out of range. For example, in some embodiments of System 100, one or more sensors, controllers, and sensor-controller hybrids may be unable to directly communicate with the router as a result of distance. Likewise, in some embodiments of System 200, one or more sensors may be outside of the hub's range. Under those circumstances, in some embodiments, two or more devices may form an ad-hoc or decentralized network. In some embodiments, data may be communicated amongst a group, sequence, or collection of devices until it reaches a device that is within range. For example, in some embodiments of System 100, one sensor, controller, or sensor-controller hybrid may communicate with one or more other sensors, controllers, or sensor-controllers over a wireless link (e.g., WiFi, sub-GHz, ZigBee, Bluetooth) rather than directly with the router. In some embodiment of System 100, data may be passed along various sensors, controllers, or sensor-controller hybrids until it is within the range of the router. In a similar fashion, in some embodiments of System 200, one sensor may communicate with one or more other sensors over a wireless link (e.g., WiFi, sub-GHz, ZigBee, Bluetooth) instead of with the hub, forming an ad-hoc or decentralized network such that data is forwarded from one sensor to another sensor until it is within the range of the hub. In some embodiments of System 100 or 200, an ad-hoc or decentralized network may be used as described above for other reasons, such as to minimize power consumption in transmitting data.

Figure 3:
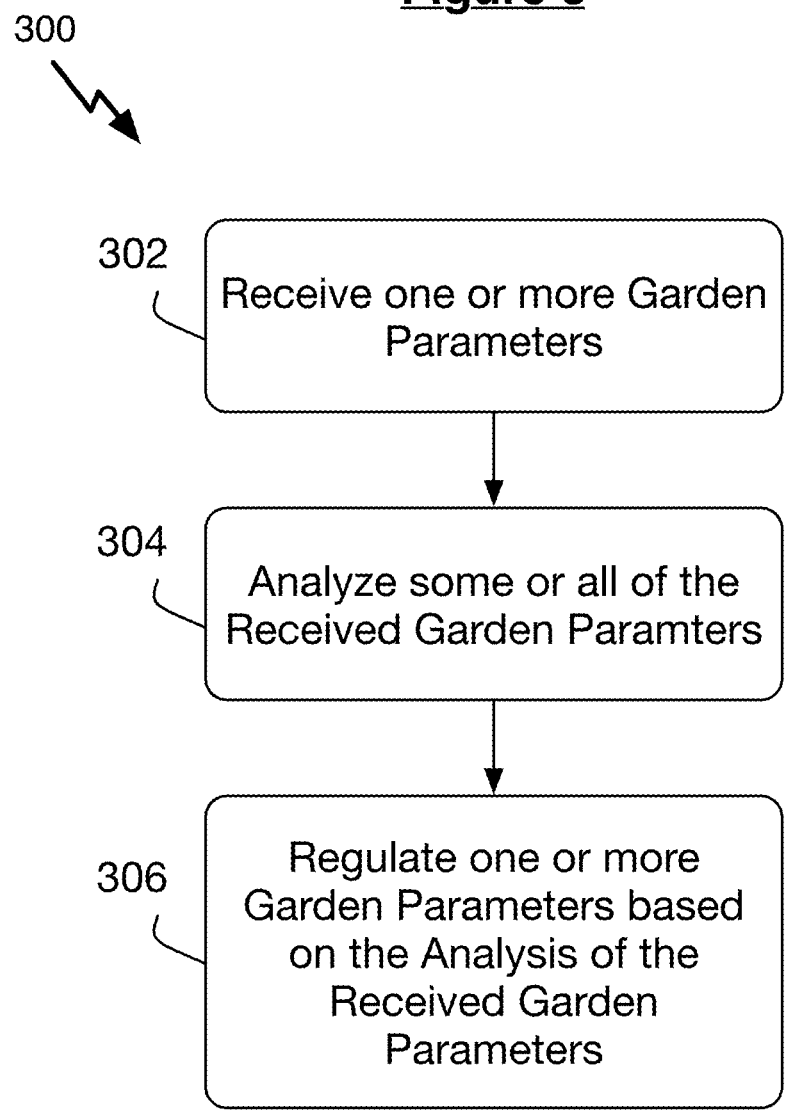
FIG. 3 is a flowchart illustrating an embodiment of a process for dynamically collecting, analyzing, and regulating garden parameters.

FIG. 3 is a flowchart illustrating an embodiment of a Process 300 for dynamically collecting, analyzing, and regulating garden parameters. In various embodiments, Process 300 may be performed by or at a cloud platform such as Cloud Platform 110 or Cloud Platform 210.

At 302, one or more garden parameters may be received. In various embodiments, the garden parameters received at the cloud platform may originate from one or more sensors (e.g., Sensor 140, Sensor 250) or sensor-controller hybrids. As discussed earlier, sensors (e.g., Sensor 140 and Sensor 250) as well as sensor-controller hybrids may be capable of measuring various garden parameters. In various embodiments, the garden parameters received at the cloud platform may originate from sensors that are installed in one or more different gardens. In various embodiments, garden parameters may include but are not limited to soil moisture, soil salinity, soil temperature, soil pH, external temperature, external humidity, and light exposure.

At 304, some or all of the garden parameters received at 302 may be analyzed. In various embodiments, one or more statistical analysis techniques may be applied. At 306, one or more garden parameters may be regulated based at least in part on the analysis of the received garden parameters. In various embodiments, regulating garden parameters may include changing or adjusting one or more current garden parameters in a garden. For example, in some embodiments, the cloud platform may analyze data including garden parameters from one or more gardens, weather forecast, and user inputs to determine whether or not to turn on (or off) one or more sprinkler valves, and for how long. In some embodiments, turning on (or off) sprinkler valves for a certain period of time may cause desired or necessary changes in one or more garden parameters. For example, if one or more garden parameters (e.g., soil moisture, external humidity) indicate that the conditions in a garden are too arid, then the cloud platform may turn on one or more sprinkler valves for a certain amount of time in order to alleviate the aridity. Alternately or in addition, in some embodiments, the cloud platform may analyze data including garden parameters from one or more gardens, weather forecast, and user inputs to determine that the garden requires changes that entail human intervention, such as the addition of additives (e.g., fertilizer) and the application of mulch and other coverings. In some embodiments, the cloud platform may be configured to transmit an alert, notification, or recommendation to the user to perform the necessary actions.

Calibration and Optimization

As discussed with respect to FIG. 1 and FIG. 2, in various embodiments, the systems and methods described herein may utilize one or more sensors (e.g., Sensor 140, Sensor 250) or sensor-controller hybrids that are capable of measuring a variety of garden parameters. Examples of garden parameters include but are not limited to soil moisture, soil salinity, soil temperature, soil pH, external temperature, external humidity, and light exposure. In various embodiments, a sensor (or sensor-controller hybrid) may be configured to take measurements according to a predetermined or to a dynamically generated schedule or frequency. For example, in some embodiments, the sensor may be configured to take measurements at preset intervals (e.g., hourly, daily, weekly). In some embodiments, the sensor may be configured to take measurements at dynamically determined intervals. In particular, in some embodiments, the sensor may be configured to take measurements according to a dynamically generated schedule or frequency that is optimized based on specific garden conditions. For example, conditions in some gardens are volatile and change frequently while the conditions in other gardens remain relatively stable over time. Moreover, it is also often the case that some garden parameters fluctuate more frequently than others. Therefore, in some embodiments, the sensor may be configured to take the minimum number of measurements necessary to capture and provide an accurate and comprehensive range of data.

In some embodiments, a cloud platform (e.g., Cloud Platform 110, Cloud Platform 220) may receive data from the sensor that includes the various measurements taken by the sensor. In some embodiments, based on characteristics or patterns associated with the data, particularly over time, the cloud platform may be able to determine when or how frequently the sensor should optimally take its measurements. In some embodiments, data patterns or characteristics may include volatility and fluctuations that are best observed from a data set that is collected over a more extended period of time. In some embodiments, the cloud platform may develop a data profile that is specific to each garden. In some embodiments, the data profile for a garden may be built using data that includes past or historical garden parameters (i.e., different garden parameters that are collected over a period of time). Thus, in various embodiments, the cloud platform may be able to detect patterns or characteristics that indicate various levels of fluctuation or volatility based on the data profile for each garden. Thus, in some embodiments, based on data characteristic or patterns, the cloud platform may send commands or instructions to the sensor to take one or more measurements. In some embodiments, based on data characteristics or patterns, particularly with respect to individual garden parameters, the cloud platform may instruct or command the sensor to measure different garden parameters according to different schedules or frequencies. In various embodiments, the schedule or the frequency for the sensor to take measurements may be updated, adjusted, or refined as more data is collected over time and added to a garden's data profile.

As discussed earlier, sprinkler systems are typically set up into different zones. As such, in various embodiments, the sprinkler valve(s) (e.g., Valve 170, Valves 281-283) in each zone may be controlled separately based at least in part on the varying conditions in each zone. In various embodiments, regardless of the size of the garden and the number of zones, any appropriate, required, or desired number of sensors or sensor-controller hybrids may be deployed. For example, one user may install one sensor in each zone or multiple sensors in each zone. In particular, in some embodiments, one sensor can be shared across multiple zones (i.e., used in two or more zones). Advantageously, the portability and mobility of sensors and sensor-hybrids across different zones allow the various embodiments of the systems and the methods described herein to be implemented with a minimal amount of equipment, cost, and effort. Suppose, for example, that Alice wants to purchase and use only one sensor to measure garden parameters in two zones (e.g., Zone A, Zone B) in her backyard. In various embodiments, Alice may install an application (e.g., Application 190, Application 293) onto her smartphone or any other type of computing and communication device (e.g., personal computer, tablet PC). In various embodiments, using the application, Alice may input or otherwise indicate to the cloud platform the current zone that the sensor is in. Furthermore, in various embodiments, Alice may use the application to input or otherwise indicate to the cloud platform whenever the sensor is moved from one zone to another (e.g., from Zone A to Zone B, and vice versa). In those embodiments where a single sensor is used across multiple zones, the cloud platform may attribute garden parameters to the correct zone based on inputs or indications from the user. To continue the example, based on Alice's input or indication that the sensor is in Zone A, the cloud platform may attribute garden parameters received from the sensor to Zone A and not Zone B.

User Interactivity—Plant Recommendation

As discussed earlier, in various embodiments, users may communicate with the cloud platform (e.g., Cloud Platform 110, Cloud Platform 210) via the application (e.g., Application 190, Application 293), including by sending, receiving, and otherwise interacting with various types of data. Also as discussed earlier, in various embodiments, the cloud platform (e.g., Cloud Platform 110, Cloud Platform 210) may receive and analyze a variety of different types of data, including but not limited to data from sensors or sensor-controller hybrids (e.g., garden parameters from different users and gardens), weather forecast, user inputs, etc. In addition, the cloud platform may store at least a portion of the data to develop current and historical data profiles for a variety of different entities or groups of entities, including but not limited to different users, gardens, neighborhoods, regions, etc. In fact, in various embodiments, the cloud platform may be able to analyze, process, and store data in any appropriate manner, including but not limited to applying statistical analysis techniques such as aggregating, segmenting, averaging, interpolating, and extrapolating the data.

In various embodiments, the cloud platform may be able to recommend plant selections for a user. In some embodiments, the cloud platform may deliver its recommendations to the user via the application. In some embodiments, the cloud platform may determine an appropriate plant selection based on garden parameters from one or more sensors in the user's garden. For example, the appropriate plant selection may be determined based on current, historical, or predicted garden parameters from the user's own garden. Alternately or in addition, in some embodiments, the appropriate plant selection may be determined based on the type(s) of plants that have been successfully grown in a reference area, which includes but is not limited to identical, similar, or adjacent area(s). In various embodiments, based on criteria that include but are not limited to the availability or volume of data, the cloud platform may further determine an appropriately sized or situated reference area in order to determine an appropriate plant selection for a user's garden.

In some embodiments, in addition to garden parameters, the cloud platform may determine an appropriate plant selection further based on user preferences. In various embodiments, the user may stipulate his or her preferences at any level of specificity and based on any appropriate type of parameters (e.g., plant characteristics such as color, size, required maintenance). For example, Alice may indicate to the cloud platform (via the installed application) that she likes or prefers a specific type or species of peony (e.g., Chinese or Japanese peony). Alternately, Alice may indicate to the cloud platform that she likes or prefers plants that bear pink colored flowers. Based on the stated preference, the cloud platform may, in some embodiments, recommend plants that are appropriate for the user's garden. However, it can often be the case that a user indicates a preference for a plant or type of plant that is not appropriate given the user's garden parameters. Thus, in some embodiments, the cloud platform may recommend plant alternatives that are more ideal or better suited for the user's garden (i.e., plants that can survive or thrive based on the garden parameters from the user's garden) and which are similar to the preferred plant or type of plant. In some embodiments, the cloud platform's suggestions or recommendations may be displayed, via the application, in order of each plant's level of similarity to the preferred plant or type of plant. In some embodiments, the cloud platform's plant suggestions or recommendations may be displayed, in addition or instead, in order of the likelihood for each of the suggested plants to survive in the user's garden. In some embodiments, the cloud platform's plant suggestions or recommendations may be displayed with an option (e.g., a hyperlink) for the user to be directed to one or more e-commerce websites (e.g., Amazon.com®, Lowe's®, HomeDepot) that sells, carries, or can otherwise provide the plant(s).

In some embodiments, in addition to or instead of displaying plant suggestions or recommendations, the user may be given an option to enroll (via the application) in a plant subscription program (e.g., seed or plant of the month). In some embodiments, enrollment in the plant subscription program entitles the user to a regularly scheduled (e.g., monthly, quarterly) delivery of plants or seeds that may be curated from the cloud platform's plant suggestions or recommendations. In some embodiments, the cloud platform may determine and deliver (via the application) advertisements and links to other services (proprietary or thirdparty) that are appropriate to the user based on the user's garden parameters (e.g., soil quality) and inputs (e.g., preferred plants).

In some embodiments, the cloud platform may determine an appropriate plant selection based on the user's budget. In various embodiments, the cloud platform may take into consideration the user's budget in addition to or instead of the user's stated preferences. In various embodiments, the user's budget may include a one-time, initial setup cost. That is, the user may specify how much he or she can or would like to spend on plants and seeds for a garden. In various embodiments, the user's budget may further include a maintenance cost. For example, the user may specify, in addition to or instead, how much he or she can or would like to spend on maintaining the plants in the garden (e.g., water, fertilizer, mulch, etc.).

As discussed earlier, the cloud platform may use a variety of data (e.g., garden parameters, weather forecast, user inputs, etc.) to determine and to generate data indicating when the sprinkler system in a user's garden should be open (and closed). In some embodiments, the cloud platform may send commands or instructions to automatically turn on (and off) some or all of the valves in the sprinkler system. In some embodiments, the cloud platform may send instructions to the user to manually turn on (and off) some or all of the valves in the sprinkler system. In various embodiments, the cloud platform may collect and analyze a variety of data, including but not limited to current (e.g., the latest set of garden parameters), historical (e.g., garden parameters measured over a certain period time), and forecasted data (e.g., weather forecast, extrapolated garden parameters). In various embodiments, the cloud platform may collect and analyze data from a variety of sources, including but not limited to data collected by sensors in the user's garden (e.g., Sensor 140, Sensor 250), data collected by sensors in other users' gardens, weather forecast, and user feedback (e.g., real life observations of garden parameters and plant conditions). Thus, in various embodiments, the cloud platform may be capable of dynamically determining and regulating the conditions in a user's garden based on current, historical, and forecasted data. In various embodiments, a user may use the application to instruct the cloud platform to emulate or recreate the garden parameters in another user's garden. In an earlier example, Alice was unable to grow the same kind of peony that thrives in her neighbor Bob's yard. Suppose both Alice and Bob have installed System 100, as described with respect to FIG. 1, or System 200, as described with respect to FIG. 2. In this case, the cloud platform would have access to garden parameters from both Alice and Bob's gardens. The garden parameters from Bob's garden have proven to be conducive to cultivating peonies. As such, in some embodiments, Alice can instruct the cloud platform to regulate or modify her garden parameters, including by turning on and off one or more sprinkler valves and recommending one or more actions on the part of Alice (e.g., fertilizer, mulch, coverings), so that the garden parameters in Alice's garden match the garden parameters in Bob's garden.

In various embodiments, the cloud platform (e.g., Cloud Platform 110, Cloud Platform 210) may be configured to continuously interact with a user, a garden, and a microclimate (i.e., the regional environment and characteristics of the user's garden). In various embodiments, a control system may be paradigmatic of the interactions and the nexus between the cloud platform, the user, the garden, and the microclimate.

Figure 4:
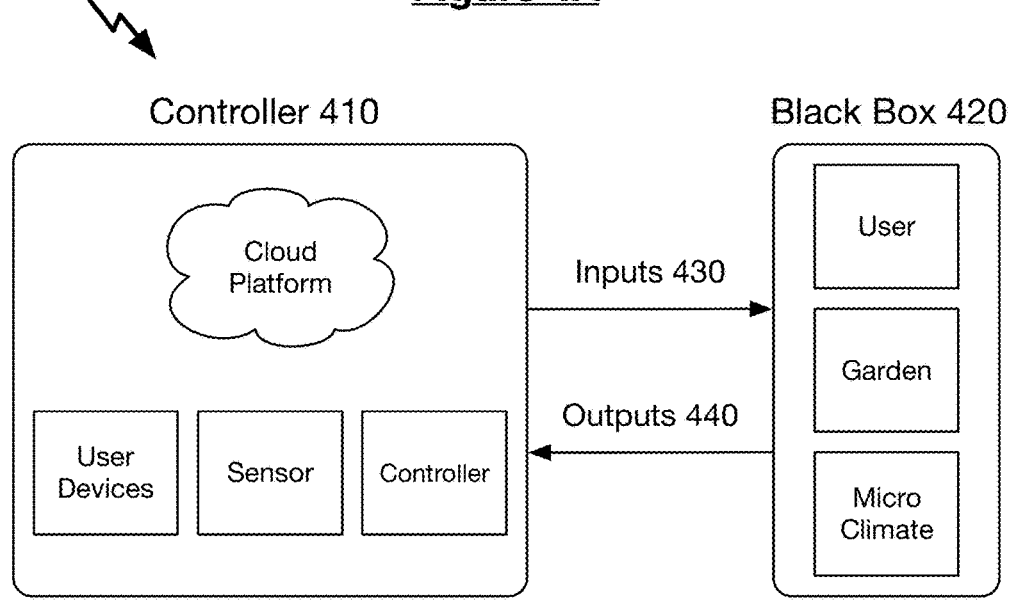
FIG. 4A is a diagram illustrating an embodiment of a control system.
FIG. 4B is a flowchart illustrating an embodiment of a process for making plant recommendations.

FIG. 4A is a diagram illustrating a Control System 400. As shown in FIG. 4A, in various embodiments, Control System 400 may comprise a Controller 410 and a Black Box 420. In various embodiments, Controller 410 may correspond to the system for dynamically collecting, analyzing, and regulating garden parameters (e.g., System 100, System 200) described herein. As described with respect to FIG. 1 and FIG. 2, various embodiments of the system for dynamically collecting, analyzing, and regulating garden parameters may include some combination of the following components: a cloud platform (e.g., Cloud Platform 110, Cloud Platform 220), sensors (e.g., Sensor 140, Sensor 250), user devices (e.g., Devices 181-182, Devices 291-292), and a hub (e.g., Hub 240) or valve controllers (e.g., Controller 150). Meanwhile, in various embodiments, Black Box 420 represents a typical garden ecosystem containing a user (e.g., Alice), a garden (e.g., Alice's garden), and a microclimate (e.g., Mission Valley in San Diego, Calif.). In various embodiments, Controller 410 may be configured to determine inputs (e.g., Inputs 430) into Black Box 420 based on the outputs (e.g., Outputs 440) from Black Box 420. In various embodiments, Inputs 430 from Controller 410 may include a variety of data that can be used to and is otherwise capable of altering conditions inside Black Box 420. In various embodiments, Outputs 440 may include a variety of data that is indicative of the conditions inside Black Box 420, including but not limited to readings, measurements, and feedback from the different constituents of Black Box 420 (e.g., the user, garden, and microclimate). In various embodiments, Controller 410 may continuously refine Inputs 430 based on Outputs 440 in order to determine a set of inputs that yields one or more ideal, desired, expected, or required outputs. In various embodiments, Controller 410 may determine a set of inputs that yields the ideal, desired, expected, or required outputs by satisfying requirements or conditions imposed by some or all of the constituents of Black Box 420. In various embodiments, Controller 410 may determine a set of inputs that would improve, influence, and otherwise change the current conditions in Black Box 420 (as indicated by a previous set of outputs) so that the next set of outputs from Black Box 420 would approximate or match the ideal, desired, expected, or required outputs.

For example, in some embodiments, users may have certain characteristics, which are typically manifest as one or more preferences for certain plants or for a particular budget. Meanwhile, in various embodiments, the user's garden may also exhibit a number of characteristics. Characteristics of the garden may be, in some embodiments, captured in the garden parameters measured by various sensors or in the user's observations. Finally, in some embodiments, the microclimate may host a variety of characteristics as well, including weather conditions such as sun, snow, rain, high winds, etc. Thus, in various embodiments, Outputs 440 may include readings and measurements of some or all of the characteristics of the constituents of Black Box 420. For example, in some embodiments, Outputs 440 may include but is not limited to user input, weather (e.g., current and forecasted), and various measured garden parameters. Based on Outputs 440, in various embodiments, Controller 410 may determine Inputs 430, which may include, as examples, commands and instructions to open (and close) sprinkler valves, and alerts, notifications, and recommendations to the user to perform one or more actions (e.g., water, fertilize, apply mulch, cover plant, etc.). As FIG. 4A shows, in the various embodiments Control System 400, Controller 410, and Black Box 420 may be part of an iterative feedback loop. On the one hand, in various embodiments, Inputs 430 may both regulate and continuously evolve based on Outputs 440. On the other hand, Outputs 440, in various embodiments, may both change as a result of Inputs 430 and perpetuate the evolution of Inputs 430.

FIG. 4B is a flowchart illustrating an embodiment of a Process 401 for making plant recommendations. In various embodiments, Process 401 may be performed by or at a cloud platform (e.g., Cloud Platform 110, Cloud Platform 210). At 402, at least one plant selection criterion may be received. In various embodiments, plant selection criteria may originate from a number of different sources, including but not limited to sensors installed in the user's garden, and plant or budget preferences specified by the user.

At 404, at least one plant to recommend may be determined based at least in part on the selection criteria. For example, in some embodiments, the cloud platform may determine one or more plants to recommend based on the current, historical, or forecasted garden parameters in the user's garden. Alternately or in addition, in some embodiments, the cloud platform may determine one or more plants to recommend based on preferences stated by the user, including but not limited to the user's budget and the user's preferred plant selections. Furthermore, in some embodiments, in scenarios where the user's preferred plant selections are inappropriate or unsuited for the user's garden (e.g., based on the user's current, historical, or forecasted garden parameters), the cloud platform may be able to recommend plants that are similar to the user's preferred plants but can also tolerate or thrive in the user's garden.

User Interface

In the various embodiments of the systems and methods described herein, various garden events may be converted into one or more appropriate units of accounting. In various embodiments, examples of garden events may include but are not limited to turning on the sprinkler system, rainfall, fertilizing, and applying mulch and other coverings. In particular, in some embodiments, garden events may be converted into an appropriate currency (e.g., USD, Euros) in order to reflect the expenditures and savings generated by each garden event. As one example, in various embodiments, the cloud platform (e.g., Cloud Platform 110, Cloud Platform 210) may keep track of the current status of sprinkler valves (e.g., Valve 170, Valves 281-283). Thus, in various embodiments, the cloud platform may determine when each sprinkler system was turned on and for how long. Consequently, in various embodiments, the cloud platform may estimate the amount of water that was used and convert this information into a dollar amount (e.g., it costs $5 to water Zone A for 30 minutes).

In another example, the cloud platform may be configured to send an alert, notification, or recommendation that instructs a user to perform one or more actions. In some embodiments, the alert, notification, or recommendation may further include an estimated cost associated with the instructed actions. For instance, the cloud platform may determine based on a variety of data including a difference between the current pH or salinity level of the soil, and the ideal, desired, required, or expected level(s), that a certain amount of fertilizer is needed. In some embodiments, the cloud platform's alert, notification, or recommendation instructing the user to apply fertilizer to the user's garden may include the cost for the amount of fertilizer needed.

In various embodiments, the cloud platform may also estimate the amount of savings generated by a garden event. For example, if it rained profusely one day, based on data such as the weather forecast and the level of moisture in the soil after the rain, the cloud platform may determine and indicate to the user that his or her garden will not have to be watered for at least 8 days, generating a savings of $20. In various embodiments, the cloud platform may further estimate the cost of recreating ideal garden parameters or the specific garden parameters found in another garden. In an earlier example, Alice wishes to recreate the garden parameters in Bob's garden. The cloud platform may, in various embodiments, approximate the overall or individual cost corresponding to the amount of water, fertilizer, and mulch that are required to transform the existing conditions in Alice's garden so that the two gardens would exhibit identical or near-identical garden parameters.

In various embodiments, the cloud platform may analyze various types of data and generate different metrics indicating the efficiency of a user's sprinkler system. As discussed earlier, in various embodiments, the cloud platform may be able to estimate the amount of water usage based on information regarding when the user's sprinkler system was in use. In various embodiments, the cloud platform may assess the amount of water usage relative to one or more different benchmarks, including but not limited to an ideal, desired, required, and expected set of garden parameters. Suppose, for example, that Alice's sprinkler system was turned on for a certain period time (e.g., X minutes). In some embodiments, the cloud platform may estimate what the expected level of moisture in Alice's garden should be after X minutes of watering. In some embodiments, the cloud platform's estimate may be generated based on a host of different types of data (e.g., Data 161-162, Data 261-262), including but not limited to current weather conditions (e.g., temperature, humidity, wind), historical garden parameters measurements from both Alice and other similar gardens taken before and after watering, and empirical statistics. In various embodiments, the cloud platform may determine the efficiency of Alice's sprinkler system as a measure of how close (e.g., expressed as a percentage) the moisture level in Alice's garden is to the expected moisture level. Alternately, returning again to the previous example where Alice is attempting to recreate the garden parameters in Bob's garden, in some embodiments, the cloud platform may also determine the efficiency of Alice's sprinkler system in terms of the proximity between the moisture level in her garden after X minutes of watering and the ideal moisture level found in Bob's garden.

In various embodiments, the cloud platform may also take into account the cost of utilities, such as via electric or water rates, to determine when it is most cost-efficient to operate a sprinkler system. In some embodiments, a user may be able to select a cost-efficient profile, which may cause the cloud platform to adjust how it regulates the one or more garden parameters or determines plant recommendations based on the cost of utilities. In various embodiments, the cloud platform may estimate the amount of resources from a utility that would be used for an event and convert this information into a dollar amount (e.g., it costs $5 to water Zone A for 30 minutes at 6 AM, it costs $10 to water Zone A at 2 PM). In various embodiments, the cloud platform may also take into account legal restrictions, such as water restrictions, to determine when operating a sprinkler system is permissible. In such embodiments, the cloud platform may regulate the one or more garden parameters to avoid operating a sprinkler system during impermissible times or notify a user that a legal restriction may apply to their garden for a watering time selected by a user.

Figure 5:
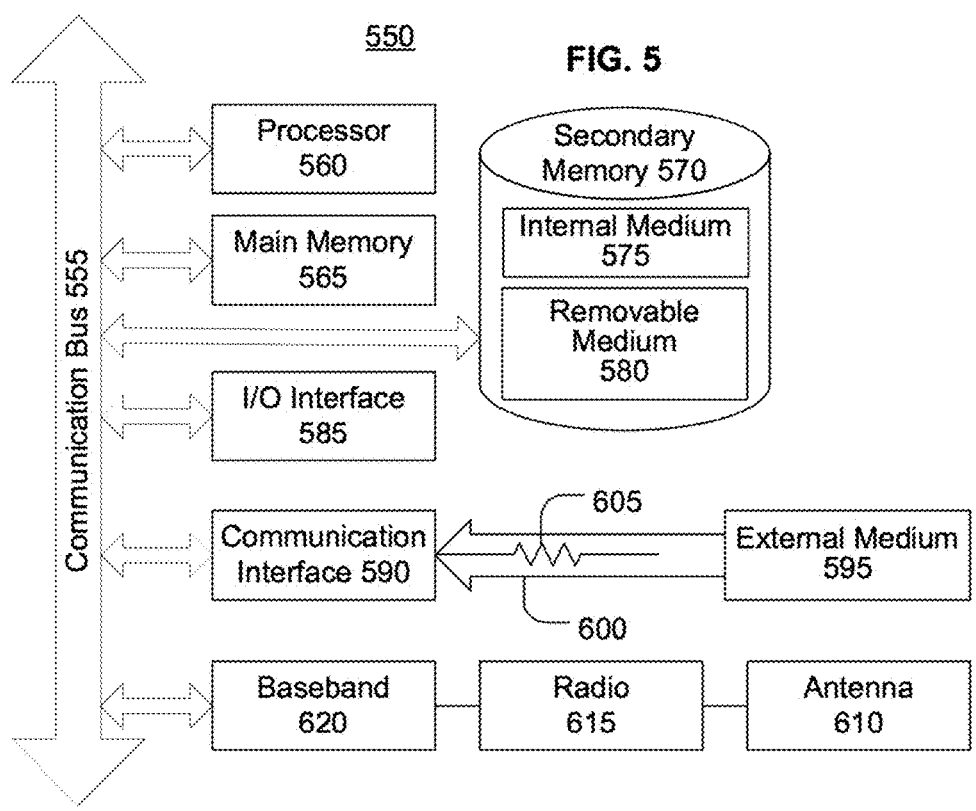
FIG. 5 illustrates an example of a computing environment including a computing device suitable for use in some embodiments.

FIG. 5 is a block diagram illustrating an embodiment of a wired or wireless System 550 that may be used in connection with the various embodiments described herein.

For example, System 550 may be used to implement Devices 181-182 as described with respect to FIG. 1, as well as Devices 291-292 and Hub 240, as described with respect to FIG. 2. In some embodiments, System 550 may be a conventional personal computer, computer server, personal digital assistant, smart phone, tablet computer, or any other processor enabled device that is capable of wired or wireless data communication. However, it is to be understood that other computer systems or architectures may be also used, as will be clear to those skilled in the art.

System 550 preferably includes one or more processors, such as Processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with Processor 560.

Processor 560 is preferably connected to a Communication Bus 555. Communication Bus 555 may include a data channel for facilitating information transfer between storage and other peripheral components of System 550. Communication Bus 555 further may provide a set of signals used for communication with Processor 560, including a data bus, address bus, and control bus (not shown). Communication Bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a Main Memory 565 and may also include a Secondary Memory 570. Main Memory 565 provides storage of instructions and data for programs executing on Processor 560. Main Memory 565 is typically semiconductor-based memory such as dynamic random access memory ("DRAM") or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

Secondary Memory 570 may optionally include an internal memory (Internal Medium 575) or a Removable Medium 580, for example a floppy disk drive, a magnetic tape drive, a compact disc ("CD") drive, a digital versatile disc ("DVD") drive, etc. Removable Medium 580 is read from or written to in a well-known manner. Removable Medium 580 may be, for example, a floppy disk, magnetic tape, CD, DVD, SD card, etc.

Removable Medium 580 is a non-transitory computer readable medium having stored thereon computer executable code (i.e., software) or data. The computer software or data stored on the Removable Medium 580 is read into System 550 for execution by Processor 560.

In alternative embodiments, Secondary Memory 570 may include other similar means for allowing computer programs or other data or instructions to be loaded into System 550. Such means may include, for example, an external storage medium (External Medium 595) and a Communication Interface 570. Examples of External Medium 595 may include an external hard disk drive or an external optical drive, or an external magneto-optical drive.

Other examples of Secondary Memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media (Removable Medium 580) and Communication Interface 590, which allow software and data to be transferred from External Medium 595 to System 550.

System 550 may also include an input/output ("I/O") interface, I/O Interface 585. I/O Interface 585 facilitates input from and output to external devices. For example I/O Interface 585 may receive input from a keyboard or mouse and may provide output to a display. I/O Interface 585 is capable of facilitating input from and output to various alternative types of human interface and machine interface devices alike.

System 550 may also include a Communication Interface 590. Communication Interface 590 allows software and data to be transferred between System 550 and external devices (e.g. printers), networks, or information sources. For example, computer software or executable code may be transferred to System 550 from a network server via Communication Interface 590. Examples of Communication Interface 590 include a modem, a network interface card ("NIC"), a wireless data card, a communications port, a PCMCIA slot and card, an infrared interface, and an IEEE 1394 fire-wire.

Communication Interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via Communication Interface 590 are generally in the form of electrical communication signals 605. These signals 605 are preferably provided to Communication Interface 590 via a communication channel 600. In one embodiment, the communication channel 600 may be a wired or wireless network, or any variety of other communication links. Communication channel 600 carries signals 605 and may be implemented using a variety of wired or wireless communication means including wire or cable, fiber optics, conventional phone line, cellular phone link, wireless data communication link, radio frequency ("RF") link, or infrared link.

Computer executable code (i.e., computer programs or software) may be stored in Main Memory 565 or Secondary Memory 570. Computer programs may also be received via Communication Interface 590 and stored in Main Memory 565 or Secondary Memory 570. Such computer programs, when executed, enable System 550 to perform the various functions as previously described.

In this description, the term "computer readable medium" is used to refer to any non-transitory computer readable storage media used to provide computer executable code (e.g., software and computer programs) to the system 550.

Examples of these media include Main Memory 565, Secondary Memory 570 (including Internal Medium 575, Removable Medium 580, and External Medium 595), and any peripheral device communicatively coupled with Communication Interface 590 (including a network information server or other network device). These non-transitory computer readable mediums are means for providing executable code, programming instructions, and software to System 550.

In an embodiment that is implemented using software, the software may be stored on a computer readable medium and loaded into System 550 by way of Removable Medium 580, I/O Interface 585, or Communication Interface 590. In such an embodiment, the software is loaded into System 550 in the form of electrical communication signals 605. The software, when executed by Processor 560, preferably causes Processor 560 to perform the inventive features and functions previously described herein.

System 550 also includes optional wireless communication components that facilitate wireless communication over a voice and over a data network. The wireless communication components comprise an antenna system (Antenna 610), a radio system (Radio 615) and a baseband system (Baseband 620). In System 550, radio frequency ("RF") signals are transmitted and received over the air by Antenna 610 under the management of Radio 615.

In one embodiment, Antenna 610 may comprise one or more antennae and one or more multiplexors (not shown) that perform a switching function to provide Antenna 610 with transmit and receive signal paths. In the receive path, received RF signals can be coupled from a multiplexor to a low noise amplifier (not shown) that amplifies the received RF signal and sends the amplified signal to Radio 615.

In alternative embodiments, Radio 615 may comprise one or more radios that are configured to communicate over various frequencies. In one embodiment, Radio 615 may combine a demodulator (not shown) and modulator (not shown) in one integrated circuit ("IC"). The demodulator and modulator may also be separate components. In the incoming path, the demodulator strips away the RF carrier signal leaving a baseband receive audio signal, which is sent from Radio 615 to Baseband 620.

If the received signal contains audio information, Baseband 620 decodes the signal and converts it to an analog signal. Then the signal is amplified and sent to a speaker. Baseband 620 also receives analog audio signals from a microphone. These analog audio signals are converted to digital signals and encoded by Baseband 620. Baseband 620 also codes the digital signals for transmission and generates a baseband transmit audio signal that is routed to the modulator portion of Radio 615. The modulator mixes the baseband transmit audio signal with an RF carrier signal generating an RF transmit signal that is routed to the antenna system and may pass through a power amplifier (not shown). The power amplifier amplifies the RF transmit signal and routes it to Antenna 610 where the signal is switched to the antenna port for transmission.

Baseband 620 is also communicatively coupled with Processor 560. The central processing unit, Processor 560, has access to the data storage areas, Main Memory 565 and Secondary Memory 570. The central processing unit, Processor 560, is preferably configured to execute instructions (i.e., computer programs or software) that can be stored in Main Memory 565 or Secondary Memory 570. Computer programs can also be received from the baseband processor, Baseband 610, and stored in Main Memory 565 or in Secondary Memory 570, or executed upon receipt. Such computer programs, when executed, enable System 550 to perform the various functions as previously described. For example, Main Memory 565 may include various software modules (not shown) that are executable by Processor 560.

Figure 6:
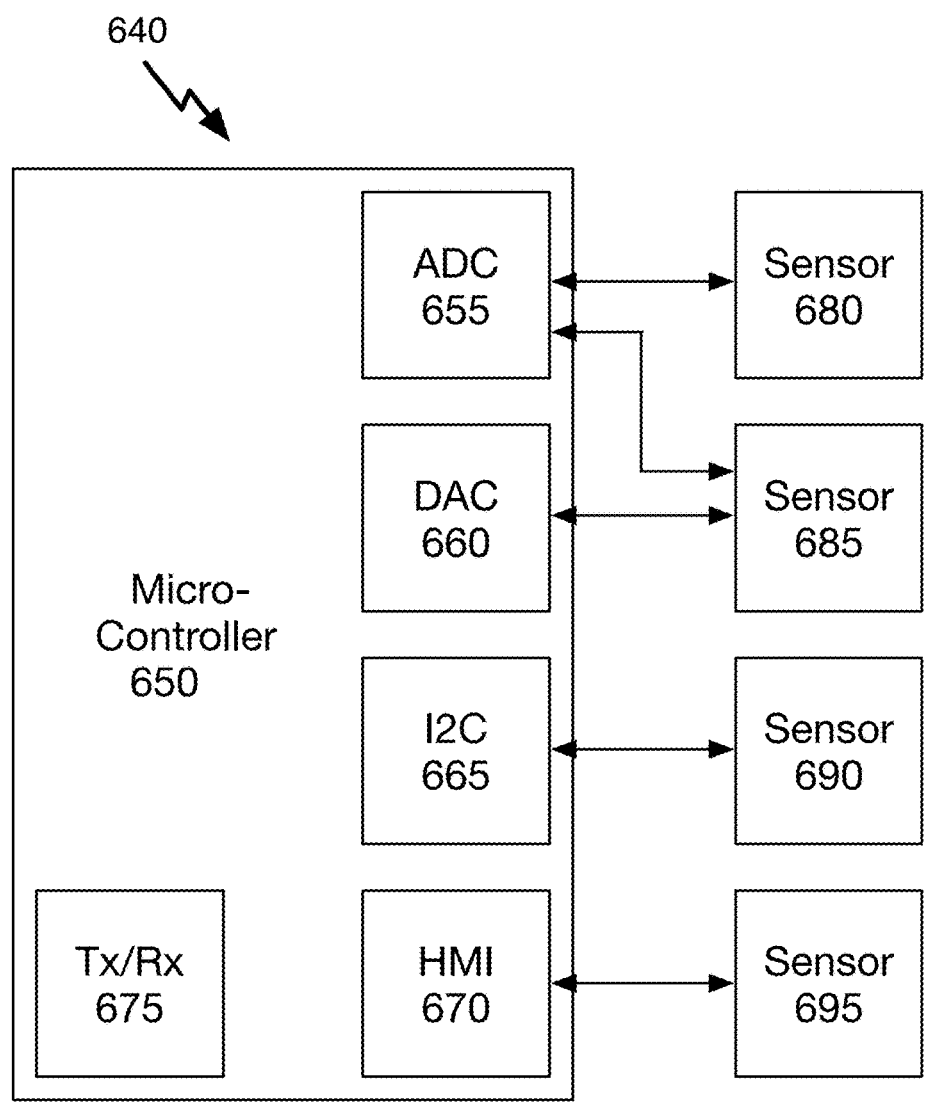
FIG. 6 illustrates an example of a sensor platform.

FIG. 6 is a block diagram illustrating an embodiment of a wireless system 640 that may be used in connection with the various embodiments described herein. For example System 640 may be used to implement Sensor 140 as described with respect to FIG. 1, as well as Sensor 250, as described with respect to FIG. 2. In some embodiments, System 640 may comprise a Microcontroller 650, which may offer integrated functions such as an analog-to-digital converter ADC 655, a digital-to-analog converter DAC 660, an Inter-Integrated Circuit interface I2C 665, a Human-Machine Interface HMI 670, and a transceiver Tx/Rx 675. In various embodiments, Microcontroller 650 may be implemented using a microcontroller manufactured by Freescale Semiconductor, Inc., such as the Freescale Kinetis KW01.

Figure 7:
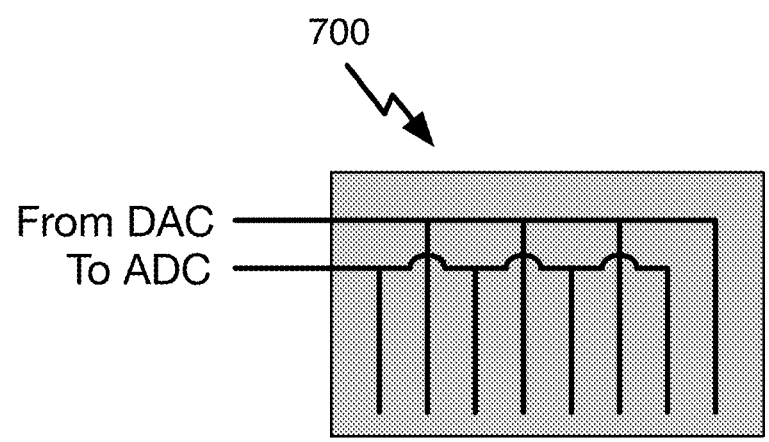
FIG. 7 illustrates an example of a sensor component for measuring the resistance of a soil.

In some embodiments, System 640 may also include one or more sensors, such as Sensor 680, Sensor 685, Sensor 690, and Sensor 695. For example, Sensor 680 may output a voltage based on a measurement of temperature, pH, or light. In some embodiments, ADC 655 may measure the voltage supplied by Sensor 680, after which Microcontroller 650 may determine the soil temperature, soil pH, or ambient light based on the voltage measurement. As another example, Sensor 685 may be comprised of a PCB 700 as shown in FIG. 7, wherein PCB 700 may be composed of interleaved traces on the PCB. The first set of traces may be connected to DAC 660 to receive a specified voltage and a second set of traces, which are not connected to the first set of traces as shown by the rounded hop-overs, may be connected to ADC 655 and a resistor of known value connected to ground. Based on the voltage applied by DAC 660 and the voltage measured by ADC 550, Microcontroller 650 may determine a soil resistance based on the voltage difference between the applied and measured voltages. In some embodiments, the applied voltage may be stepped across a range of voltages, thereby extending the dynamic range of ADC 655.

As another example, Sensor 690 may consist of an off-the-shelf temperature or humidity measurement component that can communicate with Microcontroller 650 via I2C 665.

As another example, a touch sensor is designed to accurately read small capacitive changes induced by skin on a capacitive touch screen. HMI 670 may consist of such a touch sensor, except HMI 670 may be connected to Sensor 695 that contains capacitive plates in contact with soil rather than a touch screen. By measuring the capacitance of such plates in Sensor 695 at different frequencies via HMI 670, Microcontroller 650 may determine a soil's dielectric constant. In various embodiments, Microcontroller 650 may further determine the soil's moisture content using the soil's dielectric constant, salinity, and methods known in the art (e.g., Topp et al., "Electromagnetic determination of soil water content: Measurements in coaxial transmission lines," *Water Resources Research*, June 1980).

In various embodiments, System 640 may use well-known methods in the art to support multiple sensors as described above, such as by using multiplexers/demultiplexers. Accordingly, in various embodiments, numerous sensors for different measurements may be connected to ADC 655, DAC 660, I2C 665, or HMI 670 and the use of ADC 655, DAC 660, I2C 665, or HMI 670 for obtaining measurements from one sensor does not preclude ADC 655, DAC 660, I2C 665, or HMI 670 from being used for obtaining measurements from another sensor. By using such methods well known in the art, System 640 may determine a parameterized measurement of a soil's salinity, pH, and evaporation rates based on measurements of a soil's resistance, capacitance, pH, and temperature as well as other measurements such as of ambient light, air temperature, and air humidity.

In various embodiments, System 640 may transmit the measurements from various sensors as described above to a cloud platform (e.g., Cloud Platform 110, Cloud Platform 210). The cloud platform may perform the same analysis, calibration, or other adjustments to the measurements as described herein with respect to System 640. In some embodiments, an intermediate component, such as Hub 240, Device 181, Device, 182, Device 291, or Device 292, may also perform analysis, calibration, or other adjustments based on the measurements described herein with respect to System 640. By using such methods well known in the art, the cloud platform or intermediate components (e.g., Hub 240, Device 181, Device, 182, Device 291, or Device 292) may determine a parameterized measurement of a soil's salinity, pH, and evaporation rates based on measurements of a soil's resistance, capacitance, pH, and temperature as well as other measurements such as of ambient light, air temperature, and air humidity. In various embodiments, the cloud platform or intermediate components (e.g., Hub 240, Device 181, Device, 182, Device 291, or Device 292) may then transmit results of the above analysis to System 640 or other components described herein. For example, System 640 may receive instructions to adjust future measurements based on analysis, calibration, or other adjustments from the cloud platform or intermediate components (e.g., Hub 240, Device 181, Device, 182, Device 291, or Device 292).

In some embodiments, Microcontroller 650 may also include TX/RX 675. In such embodiments, TX/RX 675 may be an 802.15.4-compliant device that has the ability to adjust its data rates and transmitter power using measurements of received signal strength from other transmitting devices. In various embodiments, TX/RX 675 may use other wireless methods such as ZigBee, Bluetooth, or WiFi.

In addition to embodiments described using software, various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit, or step is for ease of description. Specific functions or steps can be moved from one module, block, or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent presently preferred embodiments and are therefore representative of the subject matter which is broadly contemplated by the present invention. It is further understood that the scope of the present invention fully encompasses other embodiments that may become obvious to those skilled in the art and that the scope is accordingly not limited.

While various embodiments have been described above, it should be understood that they have been presented by way of example only, and not of limitation. The breadth and scope should not be limited by any of the above-described exemplary embodiments. Where this document refers to technologies that would be apparent or known to one of ordinary skill in the art, such technologies encompass those apparent or known to the skilled artisan now or at any time in the future. In addition, the described embodiments are not restricted to the illustrated example architectures or configurations, but the desired features can be implemented using a variety of alternative architectures and configurations. As will become apparent to one of ordinary skill in the art after reading this document, the illustrated embodiments and their various alternatives can be implemented without confinement to the illustrated example. One of ordinary skill in the art would also understand how alternative functional, logical or physical partitioning and configurations could be utilized to implement the desired features of the described embodiments.

Furthermore, although items, elements or components may be described or claimed in the singular, the plural is contemplated to be within the scope thereof unless limitation to the singular is explicitly stated. The presence of broadening words and phrases such as "one or more," "at least," "but not limited to," or other like phrases in some instances shall not be read to mean that the narrower case is intended or required in instances where such broadening phrases may be absent.

All references cited herein are expressly incorporated by reference.

What is claimed is:

1. A system for recommending a plant selection, comprising:
   a sever connected via a network to one or more remote devices, wherein one or more remote devices are capable of receiving or sending information between the server and one or more remote sensors or one or more remote controllers, and wherein the server is capable of:
   receiving one or more garden parameters from the one or more remote sensors, wherein the garden parameters include one or more sensor measurements of soil moisture, soil salinity, soil temperature, soil pH, external temperature, external humidity, or light exposure at one or more garden locations;
   receiving one or more plant selection criteria, wherein the one or more plant selection criteria is capable of including a plant preference or a budget preference;
   determining a plant selection based at least in part on the one or more plant selection criteria and the one or more garden parameters;
   generating a garden modification requirement if the plant selection requires an adjustment in soil moisture, soil salinity, soil temperature, soil pH, external temperature, external humidity, or light exposure at the one or more garden locations;
   sending the plant selection to at least one of the one or more remote devices;
   receiving approval of the plant selection from at least one of the one or more remote devices;
   determining a first set of instructions for the one or more remote controllers to regulate irrigation, wherein the first set of instructions includes any irrigation adjustments required to satisfy the garden modification requirement if present;
   determining a second set of instructions for the one or more remote sensors to adjust the schedule or frequency of measurements performed by the one or more remote sensors, wherein the schedule or frequency includes any adjustments to ensure accurate measurement of any desired changes in the soil moisture, soil salinity, soil temperature, soil pH, external temperature, external humidity, or light exposure at the one or more garden locations; and
   sending the first set of instructions to the one or more remote controllers, wherein the first set of instructions activates the one or more remote controllers to update their irrigation schedules, and the second set of instructions to the one or more remote sensors, wherein the second set of instructions activates the one or more remote sensors to update their measurement schedules or frequencies, if a garden modification requirement is present.

2. The system of claim 1, wherein the server is further capable of determining advertisements based on at least one of the plant selection, the plant selection criteria, or the garden parameters.

3. The system of claim 1, wherein the server is further capable of generating a plant subscription offering based on at least one of the plant selection, the plant selection criteria, or the garden parameters.

4. The system of claim 2, wherein the advertisements are capable of including a link to one or more e-commerce websites.

5. The system of claim 1, wherein determining the first set of instructions is further based on a weather forecast and a utility cost for electricity or water.

6. The system of claim 1, wherein determining the first set of instructions is further based on a weather forecast and legal restrictions constraining when irrigation can occur.

7. The system of claim 6, wherein the server is further capable of determining if an irrigation event occurs or will occur in violation of the legal restrictions and sending a notification of the violation to at least one of the one or more remote devices.

8. A computer-operable method for recommending a plant selection, comprising:
   receiving one or more garden parameters from one or more remote sensors, wherein the garden parameters include one or more sensor measurements of soil moisture, soil salinity, soil temperature, soil pH, external temperature, external humidity, or light exposure at one or more garden locations;
   receiving one or more plant selection criteria, wherein the one or more plant selection criteria is capable of including a plant preference or a budget preference;
   determining a plant selection based at least in part on the one or more plant selection criteria and the one or more garden parameters; and
   generating a garden modification requirement if the plant selection requires an adjustment in soil moisture, soil salinity, soil temperature, soil pH, external temperature, external humidity, or light exposure at the one or more garden locations;
   sending the plant selection to at least one of one or more remote devices;
   receiving approval of the plant selection from at least one of the one or more remote devices;
   determining a first set of instructions for one or more remote controllers to regulate irrigation, wherein the first set of instructions includes any irrigation adjustments required to satisfy the garden modification requirement if present;
   determining a second set of instructions for the one or more remote sensors to adjust the schedule or frequency of measurements performed by the one or more remote sensors, wherein the schedule or frequency includes any adjustments to ensure accurate measurement of any desired changes in the soil moisture, soil salinity, soil temperature, soil pH, external temperature, external humidity, or light exposure at the one or more garden locations; and
   sending the first set of instructions to the one or more remote controllers, wherein the first set of instructions activates the one or more remote controllers to update their irrigation schedules, and the second set of instructions to the one or more remote sensors, wherein the second set of instructions activates the one or more remote sensors to update their measurement schedules or frequencies, if a garden modification requirement is present.

9. The method of claim 8, further comprising determining advertisements based on at least one of the plant selection, the plant selection criteria, or the garden parameters.

10. The method of claim 8, further comprising generating a plant subscription offering based on at least one of the plant selection, the plant selection criteria, or the garden parameters.

11. The method of claim 9, wherein the advertisements are capable of including a link to one or more e-commerce websites.

12. The method of claim 8, wherein determining the first set of instructions is further based on a weather forecast and a utility cost for electricity or water.

13. The method of claim 8, wherein determining the first set of instructions is further based on a weather forecast and legal restrictions constraining when irrigation can occur.

14. The method of claim 13, further comprising determining if an irrigation event occurs or will occur in violation of the legal restrictions and sending a notification of the violation to at least one of one or more remote devices.

* * * * *